(12) United States Patent
Govindasamy et al.

(10) Patent No.: US 9,839,654 B2
(45) Date of Patent: Dec. 12, 2017

(54) ISOLATION, EXPANSION AND CHARACTERIZATION OF PRECURSOR/STEM CELLS FROM DENTAL TISSUES

(71) Applicant: HYGIEIA INNOVATION SDN BHD, Putrajaya (MY)

(72) Inventors: Vijayendran Govindasamy, Putrajaya (MY); Premasangery Kathivaloo, Putrajaya (MY)

(73) Assignee: HYGIEIA INNOVATION SDN BHD, Putrajaya (MY)

( * ) Notice: Subject to any disclaimer, the term of this patent is extended or adjusted under 35 U.S.C. 154(b) by 234 days.

(21) Appl. No.: 14/831,794

(22) Filed: Aug. 20, 2015

(65) Prior Publication Data
US 2016/0053228 A1 Feb. 25, 2016

(30) Foreign Application Priority Data
Aug. 20, 2014 (MY) .......................... PI 2014002431

(51) Int. Cl.
*A01N 1/02* (2006.01)
*A61K 35/32* (2015.01)
*C12N 5/0775* (2010.01)

(52) U.S. Cl.
CPC ............ *A61K 35/32* (2013.01); *C12N 5/0664* (2013.01); *C12N 2511/00* (2013.01)

(58) Field of Classification Search
CPC .. C12N 2513/00; C12N 5/0671; A61K 35/12; A61K 45/06; A61L 2300/64
See application file for complete search history.

(56) References Cited

U.S. PATENT DOCUMENTS 8,187,879 B2  5/2012 Laino et al.

FOREIGN PATENT DOCUMENTS

| EP | 0 251 291 B1 | 8/1991 |
|---|---|---|
| KR | 10-2008-0104274 A | 12/2008 |
| WO | 2008/129563 A2 | 10/2008 |
| WO | 2011/064733 A1 | 6/2011 |
| WO | 2012/117333 A1 | 9/2012 |

OTHER PUBLICATIONS

Andreasen, et al., "Periodontal and pulpal healing of monkey incisors preserved in tissue culture before replantation", International Journal of Oral Surgery, vol. 7, Issue 2, Apr. 1978, pp. 104-112.

Eagle, H., "Amino acid metabolism in mammalian cell cultures", Science, vol. 130, Issue 3373, Aug. 21, 1959, pp. 432-437.

*Primary Examiner* — Lynn Y Fan
(74) *Attorney, Agent, or Firm* — Maschoff Brennan

(57) ABSTRACT

A method for isolating and proliferating at least one type of precursor cell from dental origin from a single donor includes the following isolating the precursor cells from dental origin of a single donor in a sample collection media and preparing a primary stock culture. The primary stock culture is proliferated sequentially to obtain first, second and third sub-cultured stocks with cell counts ranging between $5 \times 10^6$ cells and $10 \times 10^6$ cells, $20 \times 10^6$ cells and $400 \times 10^6$ cells, $150 \times 10^6$ and $300 \times 10^6$ cells respectively. The precursor cells from the third subculture are harvested and cryopreserved to obtain a precursor cell population for cell transplantation. The dental origin of the precursor cells is from pulp, apical papilla or periodontal ligament. The precursor cell originates from mesenchymal stem cells, ectomesenchymal cells, neural stem cells, dental progenitor cells or $CD117^+$ cells.

5 Claims, 8 Drawing Sheets
(8 of 8 Drawing Sheet(s) Filed in Color)

ISOLATION, EXPANSION AND CHARACTERIZATION OF PRECURSOR/STEM CELLS FROM DENTAL TISSUES

FIELD OF TECHNOLOGY

The present disclosure relates to a method of isolation of precursor cells from a single donor. In particular, it relates to in vitro methods for isolation and large scale expansion of stem cells from dental tissues namely dental pulp stem cells from permanent teeth (DPSCs), stem cells from extracted deciduous teeth (SCDs) and stem cells from periodontal ligament tissues (PDLSCs). Further, the present disclosure also relates to sample collection media and expansion media used in these methods. Still further, the present disclosure also relates to characterization of isolated precursor/stem cell population and their use in the treatment of various disorders.

BACKGROUND OF TECHNOLOGY

Stem cells are generally defined as clonogenic cells capable of both self-renewal and multi-lineage differentiation. Post-natal stem cells have been isolated from various tissues, including bone marrow, adipose, skin, retina, and extra-embryonic tissues such as placenta, umbilical cord amniotic tissues. Along with this, dental tissue (DT) appears to be an excellent source for stem cells because it can be obtained as part of a planned serial extraction for management of occlusion. The DT can be isolated from various age groups and teeth; for example, cells isolated from dental tissue of human impacted tooth germ are known as tooth germ progenitor cells (TGPCs), stem cells from human exfoliated deciduous teeth are known as SHED, and stem cells can also be isolated from human permanent teeth (impacted molar) (DPSCs) or from apical papilla (SCAP) and periodontal ligament tissues (PDLSCs). DT offers an unlimited source of human mesenchymal stromal/stem cells (MSCs) for cell replacement/regeneration therapy as it has been shown to be multifaceted, ranging from improved recovery from stroke, cardiac ischemia to wounds and burns. However, optimal culture conditions for their long-term expansion and proliferation are necessary since large numbers of stem cells are required for therapeutic/clinical applications.

Once the precursor cells are isolated from dental tissues, maintaining their vitality is of utmost importance and various storage media have been suggested in the prior art that can be used for preserving the vitality of the isolated cells. One of the most widely used medium for storing isolated dental tissues is Eagle's Medium. Eagle's medium was first described in the article by M. Eagle, entitled "Amino acid metabolism in mammalian cell cultures", in Science, vol. 130, pages 432-437 (1959). Its specific use in preserving Monkey incisors in tissue culture before replantation has been reported by J. O. Andreasen et al, in the International Journal of Oral Surgery, vol. 7, pages 104-112 (1978). Another artificial medium for preserving or storing the isolated dental tissue is the Hanks Balanced Salt Solution. One of the foremost requirements for the artificial media for storing and preserving the isolated tissue from dental origin is that its composition should resemble with the fluids present in the isolated cells. This kind of resemblance between the composition of the storage media and the cell fluid is essential since it prevents the undue inflow or outflow of ions from the isolated cells thereby helping them maintain their vitality. In this respect, Eagle medium as well as the Hanks solutions has been proved to be effective in maintaining the vitality of the isolated dental tissue for practically significant period of time. Use of such storage media for maintaining the vitality of the periodontal membrane of the ex-articulated teeth has been disclosed in EP 0251291.

PCT Application WO 2011/064733 is directed to the isolation of human mesenchymal cells and their large scale proliferation for the purposes of obtaining a cell composition for the treatment of various diseases, teaches a medium comprising Dulbecco's Modified Eagle's Medium Knock-Out [DMEM-KO], Fetal Bovine Serum (FBS), Glutamine and Pen-Strep for collecting the isolated tissue. Further, WO 2012/117333 which specifically deals with isolation and proliferation of the DPSCs, discloses a transport medium or a preserving medium for ensuring the vitality of the isolated dental tissue before it is further subjected to expansion and proliferation. The transporting medium as disclosed in WO 2012/117333 comprises Dulbecco's Modified Eagle's Medium-Knock Out (DMEM-KO), Fetal Bovine Serum (FBS), Pen-Strep, Glutamine, Ascorbic acid and Insulin-Transferrin-Selenium (ITS).

Having isolated and stored the dental tissue, the next challenge is to amplify or expand the isolated mesenchymal cells. Again various types of media for in vitro expansion of human mesenchymal cells have been disclosed. For example, the present applicant in one of their co-pending PCT applications WO 2008/129563, have disclosed a growth media for expansion and sub-culturing the isolated mesenchymal cells that includes a basal medium comprising KO-DMEM, DMEM-LG and DMEM-F12 along with one or more of other constituents such as fetal bovine serum (FBS), growth factors, 200 niM glutamax, antibiotics, human plasma and heparin. Another PCT Application in the name of the present applicant WO2011/06733 that deals with Mesenchymal stem cells obtained from human bone marrow (hBMSCs), discloses a growth media comprising DMEM-KO supplemented with 10% FBS, 200 mM Glutamax and Pen-Strep. The requirements for the media used for expansion are different for each type of isolated tissue. Further, these requirements also vary depending on the nature of the intended differentiated tissue one intends to develop from the isolated cells. Particularly, in the context of DPSC, the present applicant in another co-pending PCT application WO 2012117333 has disclosed a xeno-free culture medium that comprises of DMEM-KO, Human Platelet Lysate (HPL), penicillin/streptomycin and Glutamine. KR 20080104274 describes a method for isolating from the follicular sack a new non-haematopoietic, mesenchymal stem subpopulation, referred to as FENC (Follicle-derived Embryonic Neural Crest stem cells), wherein variety of different media for each of type of the intended cell differentiation.

The presently known preservation media or expansion media used for isolation and expansion of precursor cells from dental origin suffer from shortcomings. Most of these media contain ascorbic acid. As is well known in the art, ascorbic acid is an extremely sensitive chemical and it is very susceptible to oxidation upon its exposure to oxygen at ambient temperature. Ascorbic acid present in these media therefore can get oxidized within a very short period of time which may even be lesser than 48 hours. The oxidized product can harm the tissues and thereby severely compromising the preservative ability of the medium. Another relatively unstable ingredient in the preservation/expansion media described above is Glutamine. At ambient temperatures, Glutamine upon degradation leads to the formation of ammonia which severely affects the preservation/expansion ability of such media. Another shortcoming of the conventionally known media used for isolation and expansion of stem cells is that they are usually prone to contamination and they are not easy to prepare and they are usually not cost-effective. Given the specific nature of the requirements for preservation and expansion of various precursor cells from dental origin, there still remains a need for a sample collection media and an expansion media that is simple, cost-effective, widely applicable and above all which ensures effective preservation of the vitality of the isolated precursor cells from the dental origin for a longer period of time with minimum chances of contamination.

Apart from the collection media, the starting material of dental tissues for the isolation of stem cells is small and it is impossible to scale up the stem cells from dental tissues at early passage using small scale flasks (T-25 cm$^2$ or T-75 cm$^2$). To overcome this caveat, the present invention introduced the large scale expansion system wherein the cells were cultured gradually from a 25 cm$^2$ area culture flask to 6360 cm$^2$ area culture flask. This resulted in more than 200 million cells than can cater for the needs for both autologous and allogeneic transplantation, considering 70-kg patients need approximately 2×10$^6$ cells/kg body weight for transplantation.

SUMMARY OF THE INVENTION

The present invention presents a method for isolating and proliferating at least one type of precursor cell from dental origin from a single donor which includes the following steps of (a) isolating the precursor cells from dental origin of a single donor in a sample collection media and preparing a primary stock culture; (b) proliferating the primary stock culture sequentially to obtain a first, second and third sub-cultured stocks with cell counts ranging between 5×10$^6$ cells and 10×10$^6$ cells, 20×10$^6$ cells and 400×10$^6$ cells, 150×10$^6$ and 300×10$^6$ cells respectively and (c) harvesting and cryo-preserving the precursor cells from the third sub-culture to obtain a precursor cell population capable of being used for cell transplantation. The dental origin of the precursor cells is at least one selected from the group consisting of pulp, apical papilla and periodontal ligament. The precursor cell is at least one selected from the group consisting of mesenchymal stem cells, ecto-mesenchymal cells, neural stem cells, dental progenitor cells and CD117$^+$ cells.

BRIEF DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
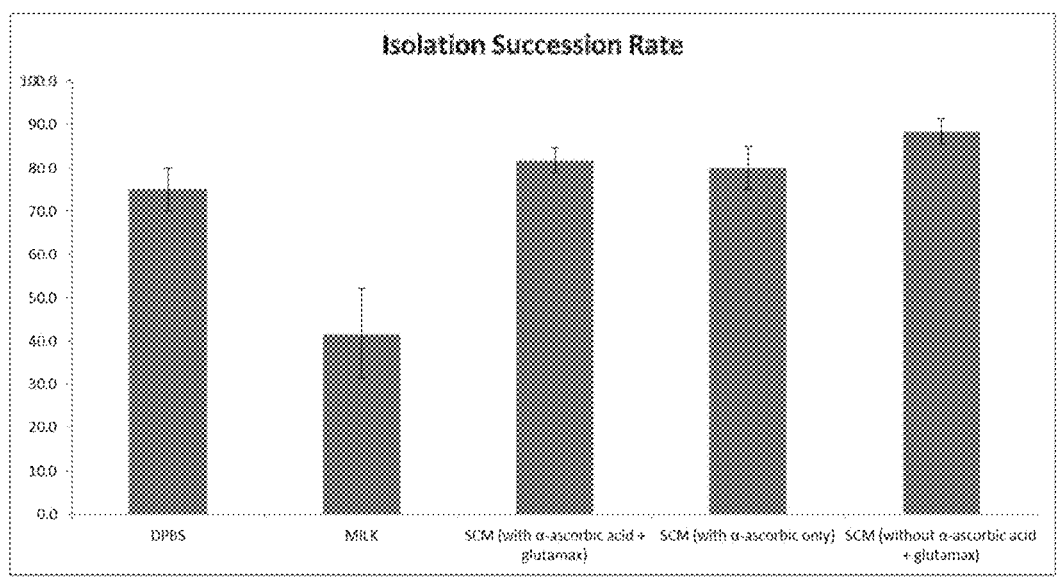
FIG. 1 refers to the percentage of cell growth succession rate using various preservation medium and determination of microbial contamination level in preservation medium (SCM I).

As used herein, the following terms and phrases shall have the meanings set forth below. Unless defined otherwise, all technical and scientific terms used herein have the same meaning as commonly understood to one of ordinary skill in the art. The term Sample Collection Media (SCM) or myCELL-Preservation Medium in the context of the present disclosures means a medium used for transferring dental tissues (pulps or ligaments) after isolation to the lab with no or minimal deterioration of the cells. SCM of the present disclosure preserve the dental tissues along with the cells associated with tissues for subsequent isolation dental pulp stem cells from permanent teeth (DPSCs), stem cells from extracted deciduous teeth (SCDs) and stem cells from periodontal ligament tissues (PDLSCs) for expansion, characterization and determination of differentiation potential in-vitro. The stem cells isolated from different source can have specific lineage and specific propensity, identification of this can help in providing a better targeted clinical application of stem cells.

In view of the potential application of stem cells from dental tissues for clinical medicine, there is growing interest in optimizing their expansion protocols so as to produce large quantities of cells for therapeutic applications, which is cost-effective and yet maintains their phenotype and functional capabilities. To date, there is inconsistency among laboratories concerning the types of media and supplementary factors for the successful isolation and expansion of stem cells from dental tissues, resulting in heterogeneous cell populations both in ex vivo experiments and in clinical trials. The present invention, overcomes the inconsistency by setting optimal culture conditions for the effective clinical-grade production of large number of stem cells from dental tissues in a short time, economizing on cost and time to serve for better cellular therapy. The results of the study are highly reproducible and consistent, making them useful for in vivo as well as in vitro manipulation without the stem cells from dental tissues losing their vigour and chromosomal stability.

Example 1

Preparation of Sample Collection Media I (SCM I) and also known as MyCELL-Preservation Medium I (a) Media Component

| Sr. No. | Media Components | Concentration | Component Composition | Example in a 50 mL |
|---|---|---|---|---|
| 1 | DMEM media* | 1 unit | 76% | 38 mL |
| 2 | Human Serum Albumin* | 5 unit | 10% | 5 mL |
| 3 | Penicillin/ Streptomycin* | 200 units mL$^{-1}$ per 200 µg mL$^{-1}$ | 2% | 1 mL |
| 4 | Fungizone* | 200 units mL–1 | 2% | 1 mL |

*commercially available reagents (b) Specification

For preservation <12 hours of tissues were extirpated from the dental tissues

Storage Temperature of Medium: 4° C.±4

Temperature of Medium upon collection of sample: 4° C.±4

Lifespan of the medium: 2 weeks (c) Cell Isolation Succession Rate using SCM I

A total of 300 tissues (20 with 2 replicates for each category) comprising of human dental pulps and periodontal ligaments were used to identify the efficacy of the SCM I. The tissues were extirpated within 2 hours and were kept in the respective media (Dulbecco Phosphate Buffer Saline (DPBS); Milk; SCM I with or without α-ascorbic acid and glutamax and SCM I with ascorbic acid alone for a period of 8 hours prior to isolation.

Isolation of Stem Cells from Dental Tissues to Produce Subculture Cell Stock-0

The isolation process was carried out in a current good manufacturing practise facility with the following parameters.

| SI NO | Parameters | Range |
|---|---|---|
| 1 | Temperature | 37° C. ± 0.5 |
| 2 | Carbon Dioxide range | 5° C. ± 0.5 |
| 3 | Room Temperature | 18° C. ± 2 |
| 4 | Relative Humidity (RH) | 55% ± 5% |
| 5 | Differential Pressure (PA) | 10 ± 10 |

A-T25 cm$^2$ culture flask was coated with 0.1% Gelatine Working Stock Solution in a Biological Safety Cabinet (BSC) that was cleaned before with sterile 70% Isopropyl Alcohol (IPA) and was exposed to UV light for 30 minutes. Dulbecco's Phosphate Buffered Saline (DPBS) (5 mL) was used to rinse the flask for one minute before the coating process. The coated flask labelled as "0.1% Gelatine Coated", was incubated at 37° C. in 5% humidified CO2 incubator for approximately 30 minutes. Excess of gelatine solution in the flask was aspirated afterwards with an aspirating pipette. Before using the flask for culturing, it was rinsed two times with 5 mL DPBS.

Seven units of 1.5 mL micro-centrifuge, labelled as numbers '1' to '7' were transferred to BSC. Tissue Washing Media (TWM) (1 mL in each tube) was then introduced into the tubes numbered 1 to 6. In the tube, labelled as "7", 0.2% Collagenase Type-IV Stock Solution and Knockout-Dulbecco's Modified Eagle Medium (KO DMEM) (1:1 ratio) (200 µL each) were mixed without frothing. A micro-centrifuge tube labelled as 'Sample" containing dental tissues (either from pulps or periodontal ligaments) in Sample Collection Media (SCM I) with sterile 70% IPA was transferred to the BSC. The collected tissue was carefully taken out from the Sample Collection Media and fractions of the tissue were inoculated to the tubes numbered '1' to '6' tube for 30 seconds. The tissue was then transferred to tube '7' which contained a mixture of 0.2% Collagenase Type-IV Stock Solution and Knockout-DMEM. The tissue was minced further with sterile scissor into tiny pieces (≈1 mm$^3$). The minced tissue was incubated at 37° C. in 5% humidified $CO_2$ incubator for 20 minutes with intermittent stirring at every 5 minutes. The tissue was further digested by adding 0.2% Collagenase Type-IV Stock Solution (500 µL) and re-incubating the resulting mixture for another 10 minutes. The digested tissue was transferred to a centrifuge tube and the Collagenase Type-IV present in the digested tissue was inactivated by diluting the digested tissue mixture with 8 mL of dental stem cells complete culture media I$^\#$ (DS-CCM I) with the following components.

| #Media composition for dental stem cells complete culture medium (DS-CCM I) | | | | |
|---|---|---|---|---|
| Sr. No. | Media Components | Concentration | Component Composition | Example in a 50 mL |
| 1 | DMEM-KO media* | 1 unit | 73% | 36.5 mL |
| 2 | Fetal Bovine Serum* | 10 units | 20% | 5 mL |
| 3 | Penicillin/ Streptomycin* | 200 units mL$^{-1}$/ 200 µg mL$^{-1}$ | 5% | 1 mL |
| 4 | Glutamax* | 1 units | 2% | 1 mL |

*commercially available reagents

The inactivated digested tissue mixture was then centrifuged 1500 rpm for 10 minutes at room temperature (18° C.±2° C.). The supernatant was discarded and the resulting pellet was re-suspended with 3 mL DS-CCM I. The cells that obtained were then transferred to the pre-coated culture flask. Another 2 mL of DS-CCM I was added to obtain a volume of 5 mL per flask. The cells were cultured in the flask by incubating them at 37° C. in 5% humidified $CO_2$ incubator for 48 hours. Thereafter, the cells were observed under inverted microscope every two days until confluency of the cells reaches up to 80%±5. At day 3, 1 mL of DS-CCM I was added to the flask by shifting it to the BSC and it was again kept back into the incubator. At day 7, the conditioned media was discarded and the flask was rinsed with 5 mL of DPBS. Another 5 mL of DS-CCM I was added to the flask by shifting it to the BSC and the flask was transferred back to the incubator. Thereafter, the conditioned media in the flask was replenished by 5 mL of DS-CCM I at every 48 hours until the cells reach 80%±5% confluency. Once it was confirmed that the cells had attained the confluency up to 80%±5%, they were labelled as Subculture Cell Stock 0 (SCS0), they were sub-cultured in the manner as provided in the next example. Determination of Cell growth was done through visualization for cell morphology.

TABLE 1

Isolation cells growth succession rate

| Various types of Preservation Medium | Rep 1 | Rep 2 | Rep 3 | Average | STDEV |
|---|---|---|---|---|---|
| DPBS | 15 | 16 | 14 | 15.0 | 1.0 |
| Milk | 9 | 6 | 10 | 8.3 | 2.1 |
| SCM I(with α-ascorbic acid + glutamax) | 16 | 16 | 17 | 16.3 | 0.6 |
| SCM I (with α-ascorbic only) | 17 | 16 | 15 | 16.0 | 1.0 |
| SCM I (without α-ascorbic acid + glutamax) | 17 | 18 | 18 | 17.7 | 0.6 |

Table 1 and FIG. 1 provides a graph that shows comparative isolation success rate using the method of the present disclosure that employs SCM I media in accordance with the present disclosure and other conventional preservation medium. A higher rate of cells (p<0.05) were obtained using SCM I media. Milk is regard as a good medium for storing tissues as they don't swell up and burst as they do when in the water. It contains proteins which keep a constant acid-alkaline ratio, anti-bacteria substances as well as the sugar to keep the tissues in intact. However, as shown in Table 1 and FIG. 1, milk is not a viable as only an average of 8 (40%) out of 20 samples were able to be grown as compared with SCM which recorded up to 17 (85%) samples. There is also no significant cell succession rate between SCM I with or without ascorbic acid or glutamax or with ascorbic acid alone. This certainly allows a reduction in the production cost.

In order to determine whether SCM I withstand to microbial contamination, the supernatant of the culture period (day 10 upon culture period) were tested for the following microbial according to the method published by World Health Organization (USP method). A total of 20 samples were used for each category.

| Aerobic Bacteria | Anaerobic Bacterium | Fungi |
|---|---|---|
| Staphylococous aureus | Clostridium sporogenes | Candida albicans |
| Bacillus subtilis |  | Aspergillus brasiliensis |
| Pseudomonas aeruginosa |  |  |

Twenty samples were used for each group and results are recorded as "pass" or "fail".

TABLE 2

Contamination level found in each cryopreservation medium.

| Groups | Rep 1 Pass | Rep 1 Fail | Rep 2 Pass | Rep 2 Fail | Rep 3 Pass | Rep 3 Fail | Average Pass | Average Fail | STDEV Pass | STDEV Fail |
|---|---|---|---|---|---|---|---|---|---|---|
| DPBS | 8 | 12 | 12 | 8 | 12 | 8 | 11 | 9 | 2.5 | 2.3 |
| Milk | 10 | 10 | 12 | 8 | 8 | 12 | 10 | 10 | 2 | 2 |
| SCM (with α-ascorbic acid + glutamax) | 17 | 3 | 17 | 3 | 18 | 2 | 17 | 3 | 0.5 | 0.5 |
| SCM (with α-ascorbic only) | 15 | 5 | 16 | 4 | 17 | 3 | 16 | 4 | 1 | 1 |
| SCM (with glutamax only) | 16 | 4 | 18 | 2 | 15 | 5 | 16 | 4 | 1.5 | 1.5 |
| SCM (without α-ascorbic acid + glutamax) | 16 | 4 | 17 | 3 | 16 | 4 | 16 | 4 | 0.5 | 1 |

Figure 2:
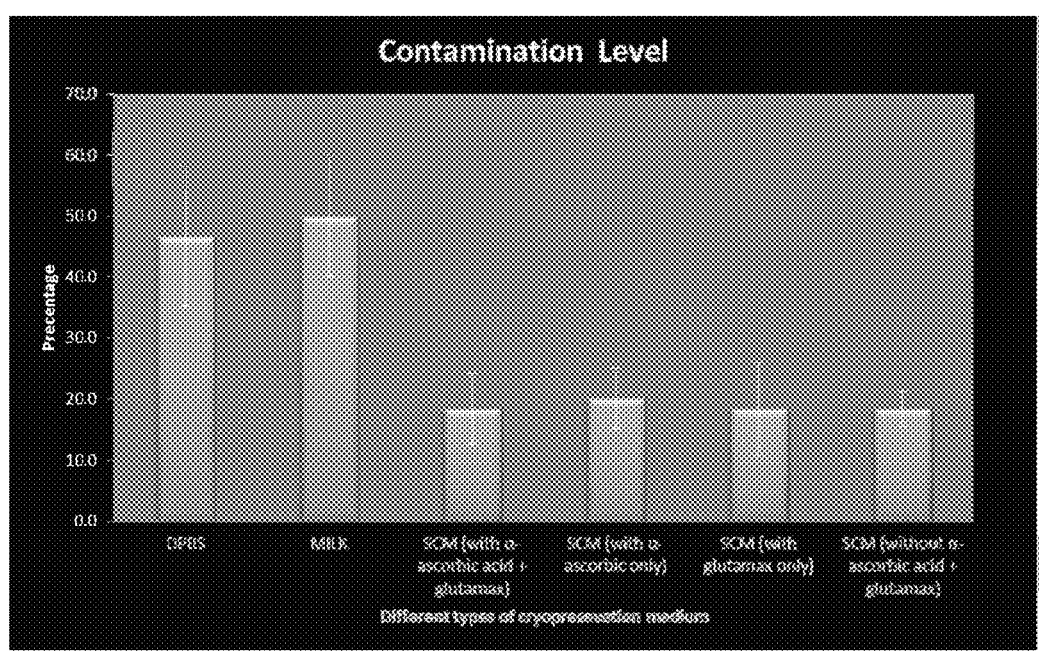
FIG. 2 refers to the percentage of contamination level found in each cryopreservation medium.

Table 2 and FIG. 2 showed that SCM I able to inhibit the growth of microbial as compared to the cryopreservation medium.

Example 2

Preparation of Sample Collection Media II (SCM II) and also known as MyCELL-Preservation Medium II (a) Media Component

| Sr. No. | Media Components | Concentration | Component Composition | Example in a 50 mL |
|---|---|---|---|---|
| 1 | DMEM media* | 1 unit | 76% | 35.5 mL |
| 2 | Human Serum Albumin* | 5 unit | 20% | 10 mL |
| 3 | Penicillin/ Streptomycin* | 200 units mL$^{-1}$/ 200 μg mL$^{-1}$ | 2% | 1 mL |
| 4 | Fungizone* | 200 units mL−1 | 2% | 1 mL |
| 5 | Insulin-Transferrin-Selenium (ITS)* | 1 unit | 5% | 2.5 mL |

*Commercially available reagents

For long term storage of sample collection media, we have modified the by increasing the concentration of human serum Albumin and added ITS. Insulin is a hormone that promotes glucose and amino acid uptake by the cell. It is thought that the mitogenic effects of insulin are due to the insulin-like growth factor receptor, IGF-1 receptor. Transferrin is an iron transport protein that functions to transport iron into the cell. The protein also serves to detoxify the medium from oxygen radicals and peroxidase. Selenium is an enzyme cofactor that activates glutathione peroxidase, a player in the detoxification of oxygen radicals.

(b) Specification

For preservation <12 hours of tissues were extirpated from the dental tissues

Storage Temperature of Medium: 4° C.±4

Temperature of Medium upon collection of sample: 4° C.±4

Lifespan of the medium: 6 months (c) Cell Isolation Succession Rate using SCM II A total of 72 tissues comprises of human dental pulps and periodontal ligaments were used to identify the efficacy of the SCM I. The tissues were extirpated within 2 hours and were kept in the DPBS (control media), SCM I and SCM II for 12, 24, 48, 72, 96, 120, 144 and 168 hours prior to isolation. The isolation was done according to method described in example 1.

TABLE 3

Percentage of cell growth succession rate using SCM II

| | 12 hours | 24 hours | 48 hours | 72 hours | 96 hours | 120 hours | 144 hours | 168 hours |
|---|---|---|---|---|---|---|---|---|
| DPBS | 75 | 60 | 50 | 50 | 50 | 30 | 20 | 0 |
| SCM I | 88 | 80 | 60 | 50 | 50 | 40 | 30 | 20 |
| SCM II | 90 | 90 | 90 | 90 | 90 | 75 | 60 | 60 |

(d) Cell Isolation Succession Rate using SCM II for a Period of 6 Months

SCM II was kept for 8 months and each month the media were used to preserve the tissues. The tissues were preserved for a period of 8 hours prior to isolation as described in example 1.

TABLE 4

Percentage of cell growth succession rate using SCM II for 7 months

| | Month 1 | Month 2 | Month 3 | Month 4 | Month 5 | Month 6 | Month 7 |
|---|---|---|---|---|---|---|---|
| SCM II | 50 | 50 | 50 | 50 | 50 | 50 | 30 |

Figure 3:
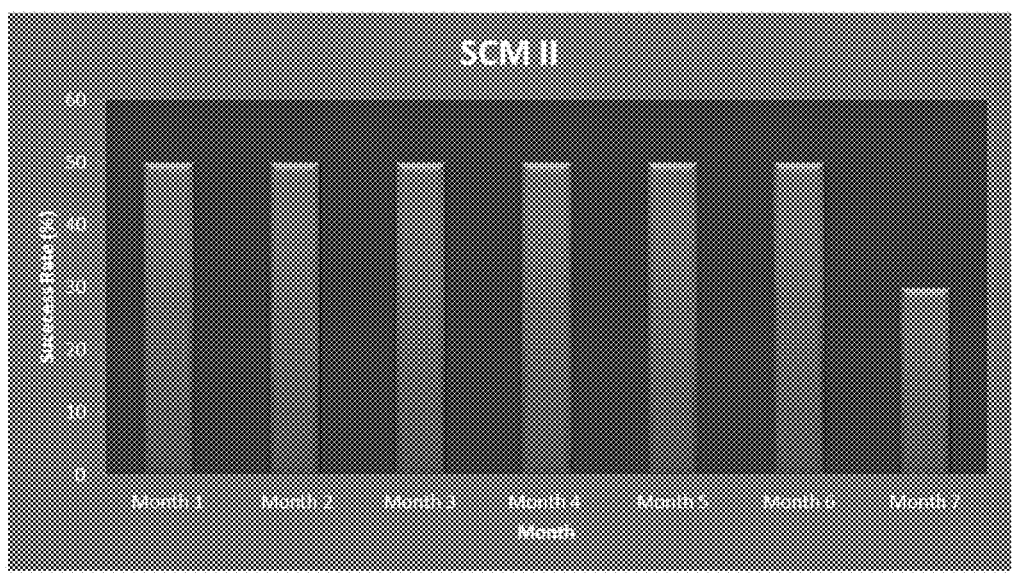
FIG. 3 refers to the percentage of cell growth succession rate using SCM II for 7 months.

Table 4 and FIG. 3 showed that SCM II able to promote cell growth for at least 6 month with a constant results. However, the percentage of succession rate was only 50%. This is due to many factors which includes the life span of each of this chemical and lot-to-lot variation on the raw materials.

Example 3

Process I: Expansion of Stem Cells from Dental Tissues (Either Periodontal Ligament or Dental Pulp) from Sub-Culture Cell Stock 0 to Subculture Cell Stock 1.

This process can be used for both autologous and allogeneic settings. One unit of the cells obtained from Example 1 was transferred to the cleaned and sterilized Biological Safety Cabinet (BSC). The conditioned media from Subculture Cell Stock 0 (SCS0) was transferred to a centrifuge tube labelled as "For QC Testing" and it was used for the purposes of quality testing. The flask carrying the cells for sub-culturing was rinsed the flask twice for 1 minute by adding Dulbecco's Phosphate Buffered Saline (DPBS) (5 mL) in the BSC. The cells were then subjected to trypsination by adding 0.05% Trypsin-EDTA (1 mL) into the flask and the flask was incubated at 37° C. in 5% humidified $CO_2$ incubator for 1-3 minutes. Complete cell detachment was confirmed by observing the flask under inverted microscope. Round floating cells as observed through the microscope indicated cell detachment. Trypsin present in the flask was neutralized by addition of dental stem cells complete culture medium## (DS-CCM II) (4 mL) which has the following components.

Media composition for dental stem cells complete culture medium (DS-CCM II)

| Sr. No. | Media Components | Concentration | Component Composition | Example in a 50 mL |
|---|---|---|---|---|
| 1 | DMEM-KO media* | 1 unit | 83% | 43 mL |
| 2 | Fetal Bovine Serum* | 10 units | 10% | 5 mL |
| 3 | Penicillin/ Streptomycin* | 200 units $mL^{-1}$ per 200 μg $mL^{-1}$ | 5% | 1 mL |
| 4 | Glutamax* | 1 units | 2% | 1 mL |

*commercially available reagents

After trypsination, the cell suspension was centrifuged at 1200 rpm for 6 minutes at room temperature (18° C.±2° C.). The supernatant was discarded and the pellet was re-suspended by adding 10 mL of DS-CCM I to the centrifuge tube. Fraction of the cell suspension (250 μL) was taken out into two separate micro-centrifuge tubes for the purposes of quality testing. One of them was sent to quality control, and the cells were counted in another using Countess Automated Cell Counter. The remainder of the cell suspension was divided into 3 units of 50 mL centrifuge tube as "QC Test Sample" ($2\times10^6$ cells), "Retention Cells" ($0.05\times10^6$ cells) and "Expansion Cells" ($0.45\times10^6$ cells). "QC Test Sample" and "Retention Cells" were centrifuged at 1200 rpm for 6 minutes at room temperature (18° C.±2° C.). The supernatant in the "QC Test Sample" was discarded and the pellet was re-suspended with 5 mL of DS-CCM II. In the same manner the supernatant in the retention cells was discarded and the pellet was re-suspended with 1 mL of Cell Freezing Media I^ (CFM I) which has the following components.

^Media composition for Cell Freezing Media

| Sr. No. | Media Components | Concentration | Component Composition |
|---|---|---|---|
| 1 | DMSO* | 100 X | 10% |
| 2 | Human Serum Albumin* | 10 units | 10% |
| 3 | Penicillin/ Streptomycin* | 200 units $mL^{-1}$/200 μg $mL^{-1}$ | 5% |
| 4 | Glutamax* | 1 units | 2% |

*commercially available reagents

The cell suspension in the cell retention sample was stored in cryogenic vials containing approximately $0.05\times10^6$ cells and the vials were transferred to a pre-cooled (+4° C.) of freezing container (Mr. Frosty). The freezing container was kept −80° C. Freezer for one and half hour to let the cells temperature reduce gradually at 1° C. per minute. After the temperature dropped below −80° C., the vials were kept into cryobox and the cryobox was shifted to vapour phase of liquid nitrogen ($LN_2$) storage freezer. In the BSC, the cells from "Expansion Cells" tube were divided into four units of T75 $cm_2$ culture flask for Subculture Cell Stock 1 (SCS1) culture each containing approximately $0.1125\times10^6$ cells and DS-CCM II (10 mL) was added to each of these stocks. The stocks were then kept for incubating at 37° C. in 5% humidified $CO_2$ incubator. The cells were monitored through inverted microscope regularly. On day 7 and 14, DS-CCM II (5 mL) was added by shifting the cells to BSC and the cells were incubated till the confluency reached 80%±5%

Example 4

Process II: Expansion of Stem Cells from Dental Tissues (Either Periodontal Ligament or Dental Pulp) from Sub-Culture Cell Stock 1 to Subculture Cell Stock 2.

This process can be used for both autologous and allogeneic settings. Process II was repeated for obtaining subculture stock 2 with following changes: The amount of trypsin used in the method step of trypsination was double (2 mL), the amount of dental stem cells complete culture medium (DS-CCM II) used for neutralizing trypsin was also double (8 mL), the amount of DS-CCM II for re-suspending the pellet after centrifugation was 20 mL, amount of cells in "QC Test Sample", "Retention Cells" and "Expansion Cells" were $3\times10^6$, $6\times10^6$ cells and $3\times10^6$ cells respectively, the amount of DS-CCM II used for re-suspending the pellet after centrifugation of "QC Test Sample" was 5 mL and the amount of Cell Freezing Media I used for re-suspending the pellet after centrifugation of "Retention Cells" was 3 mL, the Retention Cell Sample was divided into 3 cryogenic vials each one containing approximately $2\times10^6$ cells, the Expansion cells were divided into three units of 1 chamber cell stack for Subculture Cell Stock 2 (SCS2) in the BSC each containing approximately $1\times10^6$ cells, the amount of DP-CCM2 that was added before incubation was 120 mL and the amount of DS-CCM II added after day 7 and day 14 to the cell culture was 40 mL.

The resulting Subculture Cell Stock 2 (SCS2) as obtained in process III was further sub-cultured, the details of process III are provided in the following example.

Example 5

Process III: Expansion of Stem Cells from Dental Tissues (Either Periodontal Ligament or Dental Pulp) from Sub-Culture Cell Stock 2 to Subculture Cell Stock 3.

Three units of one chamber cell stacks obtained from Example 4 were transferred to the cleaned and sterilized Biological Safety Cabinet (BSC). The conditioned media from Subculture Cell Stock 2 (SCS2) was transferred to a centrifuge tube labelled as "For QC Testing" and it was used for the purposes of quality testing. The cell chambers carrying the cells for sub-culturing were rinsed twice for 1 minute by adding Dulbecco's Phosphate Buffered Saline (DPBS) (50 mL) in the BSC. The cells were then subjected to trypsination by adding 0.05% Trypsin-EDTA (20 mL per cell stack) into the flask and the cells were incubated at 37° C. in 5% humidified $CO_2$ incubator for 1 to 3 minutes. Complete cell detachment was confirmed by observing the cell chambers under inverted microscope. Round floating cells as observed through the microscope indicated cell detachment. Trypsin was neutralized by addition of dental stem cells complete culture medium (DS-CCM II) (80 mL for each cell stack). After trypsination, the cell suspension was centrifuged at 1200 rpm for 6 minutes at room temperature (18° C.±2° C.). The supernatant was discarded and the pellet was re-suspended by adding 10 mL of DS-CCM II to the centrifuge tube. Fraction of the cell suspension (250 µL) was taken out into two separate micro-centrifuge tubes for the purposes of quality testing. One of them was sent to quality control, and the cells were counted in another using Scepter Handheld Automated Cell Counter and Countess Automated Cell Counter. The remainder of the cell suspension was divided into 3 units of 50 mL centrifuge tube as "QC Test Sample" ($3\times10^6$ cells), "Retention Cells" ($46\times10^6$ cells) and "Expansion Cells" ($11\times10^6$ cells). "QC Test Sample" and "Retention Cells" were centrifuged at 1200 rpm for 6 minutes at room temperature (18° C.±2° C.). The supernatant in the "QC Test Sample" was discarded and the pellet was re-suspended with 5 mL of DP-CCM2. In the same manner the supernatant in the retention cells was discarded and the pellet was re-suspended with 23 mL of Cell Freezing Media I (CFM I). The cell suspension in the cell retention sample was stored in 23 cryogenic vials each containing approximately $2\times10^6$ cells and the vials were transferred to a pre-cooled (+4° C.) of freezing container. The freezing container was kept −80° C. freezer for one and half hour to let the cells temperature reduce gradually at 1° C. per minute. After the temperature dropped below −80° C., the vials were kept into cryobox and the cryobox was shifted to vapour phase of liquid nitrogen ($LN_2$) storage freezer. In the BSC, the cells from "Expansion Cells" tube were divided into one unit of 1 chamber cell stack ($1\times10^6$ cells) (control) and one unit of 10 chamber cell stack ($1\times10^6$ cells) for Subculture Cell Stock 3 (SCS3) and DP-CCM2 (120 mL for one member cell stack and 1200 mL for the ten member cell stack) was added to each of these stocks. The stocks were then kept for incubating at 37° C. in 5% humidified $CO_2$ incubator. The cells were monitored through inverted microscope regularly. On day 7 and 14, DS-CCM II (40 mL for each cell stack, 400 for 10 member cell stack) was added by shifting the cells to BSC and the cells were incubated till the confluency reached 80%±5%.

Example 6

Process V: Harvesting of Stem Cells from Dental Tissues (Either Periodontal Ligament or Dental Pulp) as Subculture Cell Stock 3

One unit of 1 chamber cell stack and one unit of 10 chamber cell stack containing Subculture Cell Stock 3 (SCS3) obtained from Example 5 were transferred to the cleaned and sterilized Biological Safety Cabinet (BSC). The conditioned media from Subculture Cell Stock 2 (SCS2) was transferred to a centrifuge tube labelled as "For QC Testing" and it was used for the purposes of quality testing. The cell chambers carrying the cells for sub-culturing were rinsed twice for 1 minute by adding Dulbecco's Phosphate Buffered Saline (DPBS) (50 mL for one member cell stack, 500 mL for a ten member cell stack) in the BSC. The cells were then subjected to trypsination by adding 0.05% Trypsin-EDTA (20 mL for one member cell stack, 200 mL for a ten member cell stack) into the flask and the cells were incubated at 37° C. in 5% humidified $CO_2$ incubator for 1-3 minutes. Complete cell detachment was confirmed by observing the cell chambers under inverted microscope. Round floating cells as observed through the microscope indicated cell detachment. Trypsin was neutralized by addition of dental stem cells complete culture medium (DS-CCM II) (80 mL for one member cell stack, 800 mL for a ten member cell stack). After trypsination, cell suspension from a single member cell stack was transferred to one unit of 250 mL centrifuge tube labelled as "1 CS" while the cell suspension from the ten member cell stack was transferred to four units of 250 mL centrifuge tube as "10 CS". All the tubes were centrifuged at 1200 rpm for 6 minutes at room temperature (18° C.±2° C.). The supernatant was discarded and the pellet was re-suspended by adding 50 mL of DS-CCM II to each of the centrifuge tube.

All the cell suspensions from "10 CS" tubes were transferred into one unit of 250 mL centrifuge tube, therefore the final volume of cell suspension was 200 mL. 500 µL of cells suspension from "1 CS" tube was transferred into two units of 1.5 mL micro-centrifuge tube (250 µL/tube) and they were labelled as "1 CS". In the same manner, 500 µL of cells suspension from "10 CS" tube was transferred into two units of 1.5 mL micro-centrifuge tube (250 µL/tube) and both of them were labelled as "10 CS". One unit each from "1 CS" and "10 CS" labelled tube was sent to QC Room for cell count while the cells were counted in the remaining tubes using Countess Automated Cell Counter. All the suspensions from "1 CS" centrifuge tube and "10 CS" centrifuge tube were combined into one unit of 250 mL centrifuge tube and the resultant cell suspension was centrifuged at 1200 rpm for 6 minutes at room temperature (18° C.±2° C.). The supernatant was discarded and the pellet was re-suspended by adding 50 mL of DS-CCM II. The resulting cell suspension was divided into "QC Test Sample", "Retention Cells" and "Cells for Cryobag" each containing $3\times10^6$, $15\times10^6$, $202\times10^6$ cells respectively. The "QC Test Sample" was centrifuged further at 1200 rpm for 6 minutes at room temperature (18° C.±2° C.), the supernatant was discarded and the pellet was re-suspended by adding 10 mL of DS-CCM II. The cells from "Retention Cells" and "Cells for Cryobag" tubes were suitable for cryopreservation process.

Example 7

Process VI: Cryopreservation of Stem Cells from Dental Tissues (Either Periodontal Ligament or Dental Pulp) at Subculture Cell Stock 3 as Finished Product All the materials required for cryopreservation process of Subculture Cell Stock 3 (SCS3) were transferred to the cleaned BSC including $15\times10^6$ cells suspension in one unit of 50 mL centrifuge tube labelled as "Retention Cells", five units of 1.8 mL cryogenic vial and 5 mL of Cell Freezing Media I (CFM I) after wipe with sterile 70% IPA. The cell suspension in "Retention Cells" tube was centrifuged at 1200 rpm for 6 minutes at room temperature (18° C.±2° C.). The supernatant was discarded and the pellet was re-suspended with 5 mL of CFM1. The resulting cell suspension with CFM I was divided into five units (each containing approximately $3\times10^6$ cells) of labelled 1.8 mL cryogenic vial. The labelled vials were then placed into a cryobox which was then transferred to Controlled Rate Freezer for gradual reduction of cell temperature at the rate of 1° C. Upon reaching −80° C., the cryobox was transferred to vapour phase of liquid nitrogen ($LN_2$) storage freezer.

Cryopreservation of Stem Cells from Dental Tissues (Either Periodontal Ligament or Dental Pulp) in Cryobag All the materials required for cryopreservation process of Subculture Cell Stock 3 (SCS3) were transferred to the cleaned BSC including $202\times10^6$ cells suspension in one unit of 50 mL centrifuge tube labelled as "Cells for Cryobag", one unit of cryobag, 15 mL of Cell Freezing Media I (CFM I) and one unit of cryobag. Air was removed from the cryobag using 30 mL syringe to avoid bubble-formation during cells loading. The cells in "Cells for Cryobag" were centrifuged at 1200 rpm for 6 minutes at room temperature (18° C.±2° C.). The supernatant was discarded and the pellet was re-suspended with 15 mL of CFM I. A syringe (30 mL) was loaded with 15 mL of CFMI containing approximately $202\times10^6$ cells and the syringe mouth was connected to the cryobag pin and the cryobag was filled. The cryobag thus obtained was transferred to preparation room through the pass box. The cryobag was sealed and and the excess tubing was cut using a Sterile Scissor. The cryo-bag was placed into one unit of cassette and the cassette was labelled with requisite information (Batch ID, Subculture No., No. of Cells and Date) using cryo-marker. The cassette was then transferred to Controlled Rate Freezer for gradual temperature reduction (at the rate of 1° C. per minute). Upon the temperature reaching to −80° C., the cassette was shifted to vapour phase of liquid nitrogen ($LN_2$) storage freezer.

Example 8

Morphology Images and Protein Functional Assay for Each Dental Pulp Stem Cells Isolated from Permanent (DPSCs), Deciduous (SCDs) and Periodontal Ligament Stem Cells (PDLSCs) at Subculture 3 which is also known as Finish Product.

Figure 4:
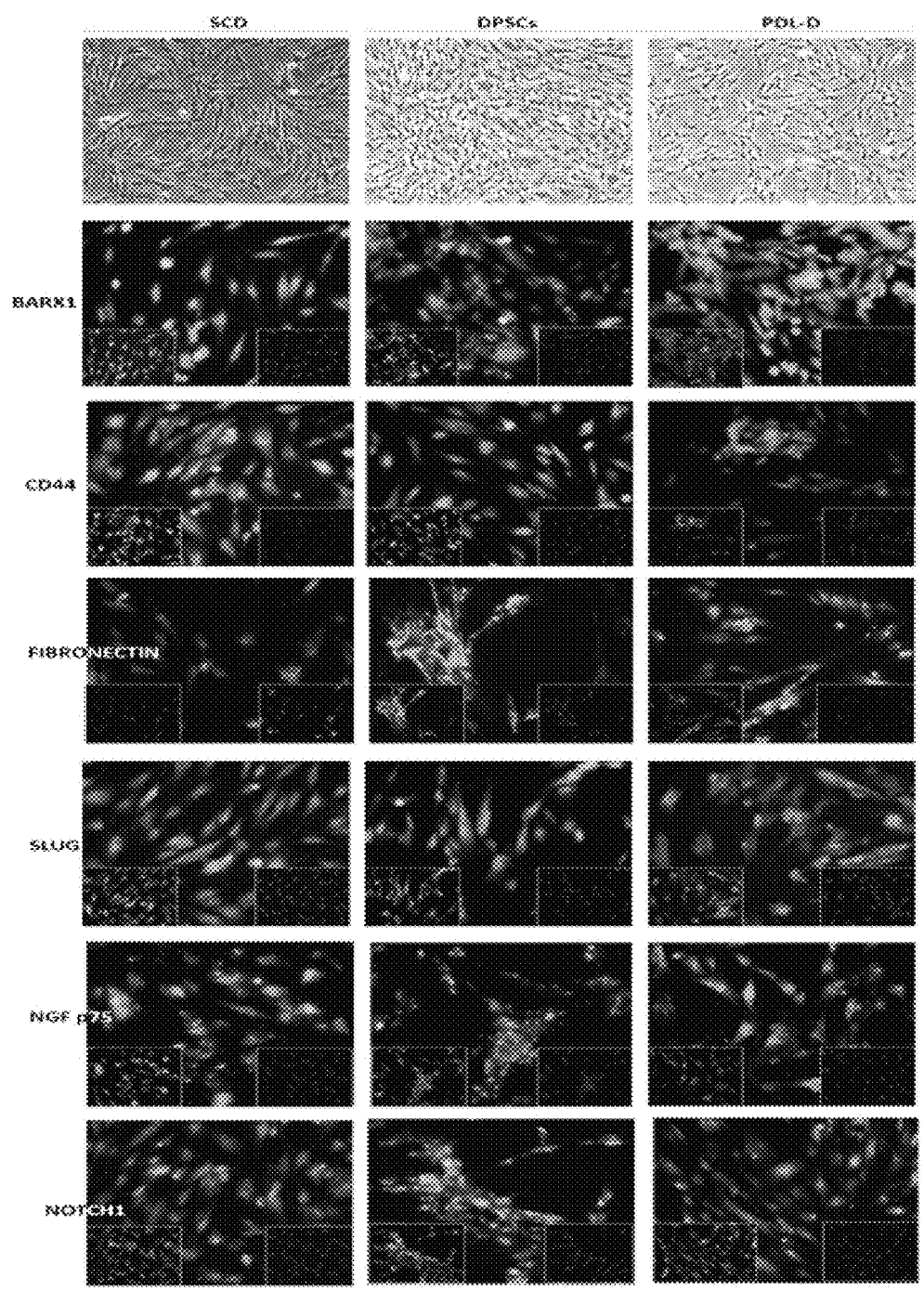
FIG. 4 refers to the morphology images and protein functional assay for each dental pulp stem cells isolated from permanent (DPSCs), deciduous (SCDs) and periodontal ligament stem cells (PDLSCs).

The morphology of the cells was taken by using an inverted microscope (Olympus) at 10× magnification. The protein functional of the cells was analysis via immunocytochemistry assay. The cells were fixed for 20 min in 4% ice cold paraformaldehyde, treated with 0.1% Triton-X for optimal penetration of cell membranes, and incubated at RT in a blocking solution (0.5% BSA; Sigma Aldrich) for 30 minutes. Primary antibodies [Barx I (mouse, Abcam), CD 44 (mouse, Abcam), 75Fibronectin (mouse, Millipore), Slug (mouse, Sigma), NGF p(rabbit, Abcam) with dilution ratio of 1:400 for all samples, except for Notch I with 1:500 ratio, were incubated overnight at 4° C., washed with Dulbecco's Phosphate Buffer Saline (DPBS; Invitrogen), and then incubated with secondary antibody (either fluorescein isothiocyanate [FITC]-conjugated IgG at RT for 90 minutes. Slides were counterstained with 4',6'-diamidino-2-phenylindole dihydrochloride (DAPI, Chemicon, Temecula, Calif., USA) for 5 min. Fluorescent images were captured by means of a Nikon-Eclipse-90i microscope (Nikon, Tokyo, Japan, http://www.nikon.com). As shown in FIG. 4, all cell lines were smaller, spindle-shaped cells and semi loosely connected cells in morphology. This is a typical characteristic of mesenchymal stem cells. Besides this, all cell lines were able to express some of the important markers related to neuro-ectoderm lineages. These include the homeobox transcription factor Barx1 was identified as a protein that binds to a regulatory element of the Ncam1 promoter. Barx1 is strongly expressed in parts of the head and neck mesenchyme, especially in parts of the first and second pharyngeal arches where it is generally restricted to neural cells-derived tissues, including mesenchyme associated with the olfactory epithelium, the primary and secondary palate, the stroma of the submandibular gland, and molar papillae. On the other hand, CD 44 involves in facilitating Schwann cell development by interacting into erbB2-erbB3 heterodimerization pathway as well signaling in response to a neuregulin. Fibronectin is a high-molecular weight (~440 kDa) glycoprotein of the extracellular matrix that binds to membrane-spanning receptor proteins called integrins. Similar to integrins, fibronectin binds extracellular matrix components such as collagen, fibrin, and heparan sulfate proteoglycans (e.g. syndecans). Likewise, NGF p75, NOTCH 1 and SLUG too plays an important role in neuroectoderm.

Colony forming unit (CFU) assay was determined by the plating of 100 cells in 35-mm dishes (BD Falcon). After 14 days in culture, the cells were removed and washed twice using DPBS (—Ca2+, —Mg2+) and fixed in 100% methanol (Sigma Aldrich, Malaysia) for 15 to 20 minutes at room temperature (23±1° C.). The cells were then stained with 0.5% crystal violet (Sigma Aldrich) for 30 minutes at room temperature (23±1° C.), followed by four times rinsing with tap water to remove the violet stain. The dish was inverted on absorbent paper and allowed to dry. Only colonies of more than 2 mm in diameter were counted. The CFU was calculated using the following formula Colony forming unit (CFU)=Total number of colonies/100

Figure 5:
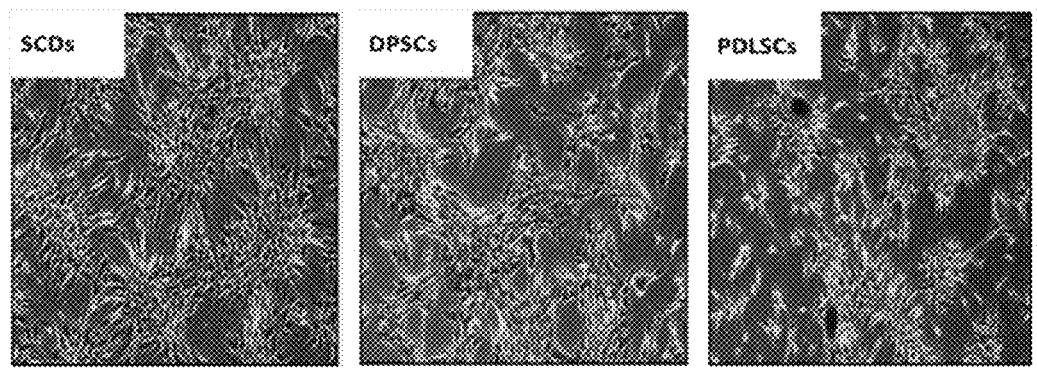
FIG. 5 refers to the Colony Forming Unit of each dental pulp stem cells isolated from permanent (DPSCs), deciduous (SCDs) and periodontal ligament stem cells (PDLSCs) at subculture 3 which is also known as finish product.
Figure 6:
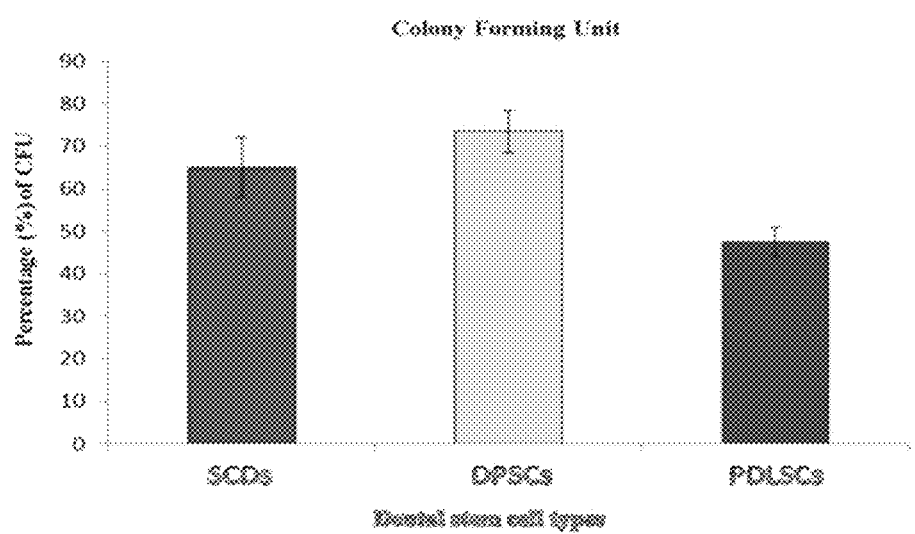
FIG. 6 refers to the percentage and mean percentage of colony forming unit.

The colony forming properties of SCDs, DPSCs, and PDLSCs were assessed at passage 3 (finish product) (refer FIG. 5). As indicated in figure below, all cell lines were able to form colonies indicating their MSC characterization. The mean percentage of colony forming unit (CFU) were higher in DPSCs (73.5±4.95) as compared with those of SCDs (65.0±7.07) and PDLSCs (47.5±3.54) as shown in FIG. 6.

Example 9

Senescence assay was performed using senescence β-galactosidase staining kit (Cell Signalling, Research Biolabs Sdn Bhd, Malaysia) as per the manufacturer's protocol. Briefly, the cells were cultivated in a 35-mm tissue culture dishes (BD Falcon) until the cells reached 80% confluence. The cells were then washed twice using DPBS (—$Ca^{2+}$, —$Mg^{2+}$) and fixed with 1× Fixative solution for 15 minutes at room temperature (23±1° C.). The cells were washed twice in DPBS (—$Ca^{2+}$ —$Mg^{2+}$) to remove 1× Fixative solution followed by stained using 1 ml Staining Solution Mixture and incubation in a humidified atmosphere 5% CO2 at 37° C. overnight. The mixture consisted of 1× Staining Solution, Staining Supplement A, Staining Solution Supplement B and 20 mg/ml X-gal in N—N-dimethylformamide. The cells were observed under a microscope at 4× magnification for evidence of blue color the following day (refer FIG. 8). The cells' senescence was calculated using the following formula:

Cells senescence=Total numbers of cell senescence/100%

Figure 7:
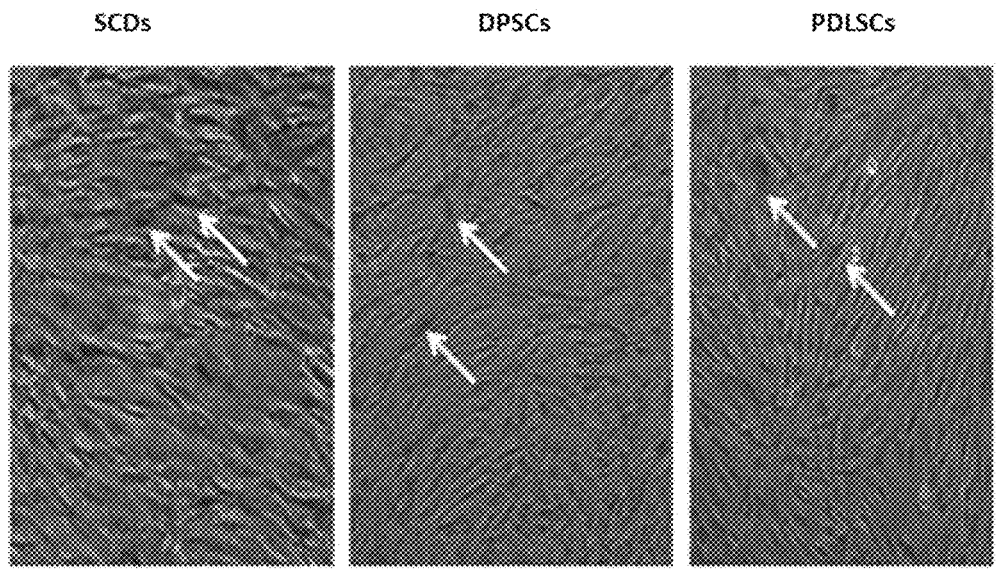
FIG. 7 refers to the β-galactosidase staining (blue) for the senescent cells at passage 3 under phase contrast microscope (magnification 10×). Senescence assay of each dental pulp stem cells isolated from permanent (DPSCs), deciduous (SCDs) and periodontal ligament stem cells (PDLSCs) at subculture (also known as passage) 3 which is also known as finish product.
Figure 8:
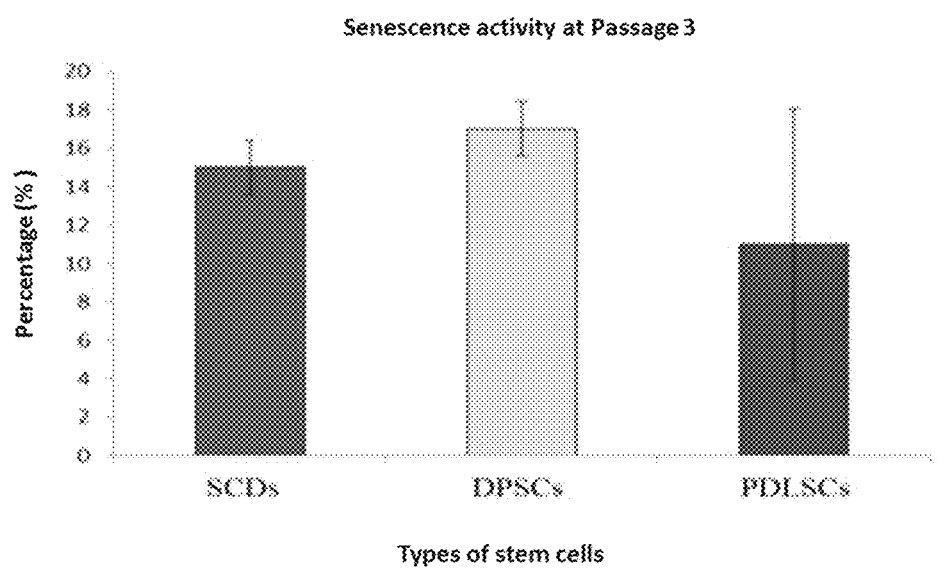
FIG. 8 refers to the mean percentage of senescence activity for dental stem cell types at passage 3.

Senescent cells were marked by β-galactosidase stains in the perinuclear area which appeared blue in colour (FIG. 7). Quantitative analysis of senescence activity revealed that senescent cells for DPSCs, SCDs, and PDLSCs were 17±1.41%, 15±1.41%, and 11±7.07%, respectively (FIG. 8)

Example 10

Figure 9:
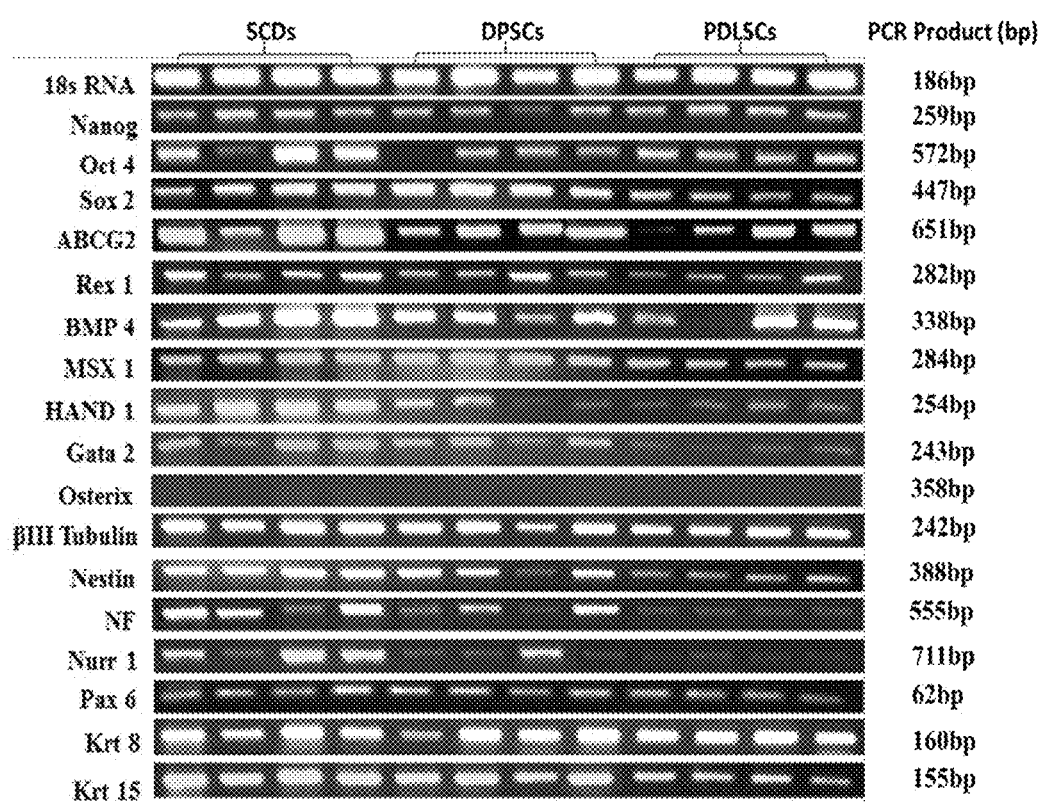
FIG. 9 refers to the RT-PCR analysis of dental stem cells showing the expressions of pluripotent and germ-layer specific markers.

Gene Expression Study of each Dental Pulp Stem Cells Isolated from Permanent (DPSCs), Deciduous (SCDs) and Periodontal Ligament Stem Cells (PDLSCs) at Subculture 3 which is also known as Finish Product (Refer FIG. 9).

The RT-PCR was performed using complementary DNA (cDNA) prepared as described in section 3.10. A total of 25 μl of PCR reaction was prepared by adding the following components; 2.5 μl of 10× PCR (—Mg2+), 1.25 μl of 50 mM MgCl2, 0.5 μL of 10 mM dNTP Mix, 1 μl of forward primer and 1 μl of reverse primer, 0.2 μl of Taq DNA polymerase, 1 μl of template cDNA and 17.55 μl of autoclaved ddH2O. The mixture was centrifuged at 500 rpm for 3 seconds. The cDNA amplification was performed at 94° C. for 5 minutes, 94° C. for 45 seconds for 30 cycles, 58.5° C. for 30 seconds for 30 cycles, 72° C. for 45 seconds for 30 cycles, and a final elongation at 72° C. for 10 minutes and 4° C. using a thermocycler. Polymerase chain reaction (PCR) products were resolved on 1.5% agarose gel which was immersed in 1× Trisborate-ethyl-enediaminetetraacetic acid (TBE) buffer. All the chemicals were purchased from Invitrogen unless stated. All the RT-PCR results were evaluated using a standard indication of gene expression as listed in Table 5. Primers for RT-PCR are listed in Table 6.

TABLE 5

Standardized indication of gene expression for RT-PCR.

| Level of Expression | Label |
|---|---|
| Very high | ++++ |
| High | +++ |
| Moderate | ++ |
| Low | + |
| Negative/No expression | − |

TABLE 6

Primers for RT-PCR

| Gene Symbol | Description | Primer Sequence (5'-3') | Base Pair |
|---|---|---|---|
| 18s | RNA, 18S ribosomal 1 | F: CGGCTACCATCCAAGGAA<br>R: GCTGGAATTACCGCGGCT | 186 |
| Rex 1 | RNA exonuclease 1 homolog | F: GCGTACGCAAATTAAAGT CCAGA<br>R: CAGCATCCTAAACAGCTC GCAGAAT | 282 |
| OCT 4 | POU class 5 homeobox 1 | F: CGACCATCTGCCGCTTTGAG<br>R: CCCCCTGTCCCCCATTCCTA | 572 |
| SOX 2 | SRY (sex determining region Y) box 2 | F: CCCCCGGCGGCAATAGCA<br>R: TCGGCGCCGGGGAGATACAT | 447 |
| NANOG | Nanog homeobox | F: CCTCCTCCATGGATCTGCTT ATTCA<br>R: TCGGCGCCGGGGAGATACAT | 299 |
| NES | Nestin | F: CAGCGTTGGAACAGAGGT TGG<br>R: TGGCACAGGTGTCTCAAG GGTAG | 388 |
| ABCG 2 | ATP-binding cassette, subfamily G, member 2 | F: GTTTATCCGTGGTGTGTC TGG<br>R: CTGAGCTATAGAGGCCTGGG | 651 |
| BMP 4 | bone morphogenetic protein 4 | F: GTCCTGCTAGGAGGCGCGAG<br>R: GTTCTCCAGATGTTCTTCG | 338 |
| MSX 1 | msh homeobox 1 | F: CCTTCCCTTTAACCCTCA CAC<br>R: CCGATTTCTCGCGCTTTTC | 284 |
| GATA 2 | GATA binding protein 2 | F: AGCCGGCACCTGTTGTGCAA<br>R: TGACTTCTCCTGCATGCACT | 243 |
| HAND 1 | heart and neural crest derivatives expressed 1 | F: TGCCTGAGAAAGAGAACCAG<br>R: AGGATGAACAAACAC | 254 |

Figure 10:
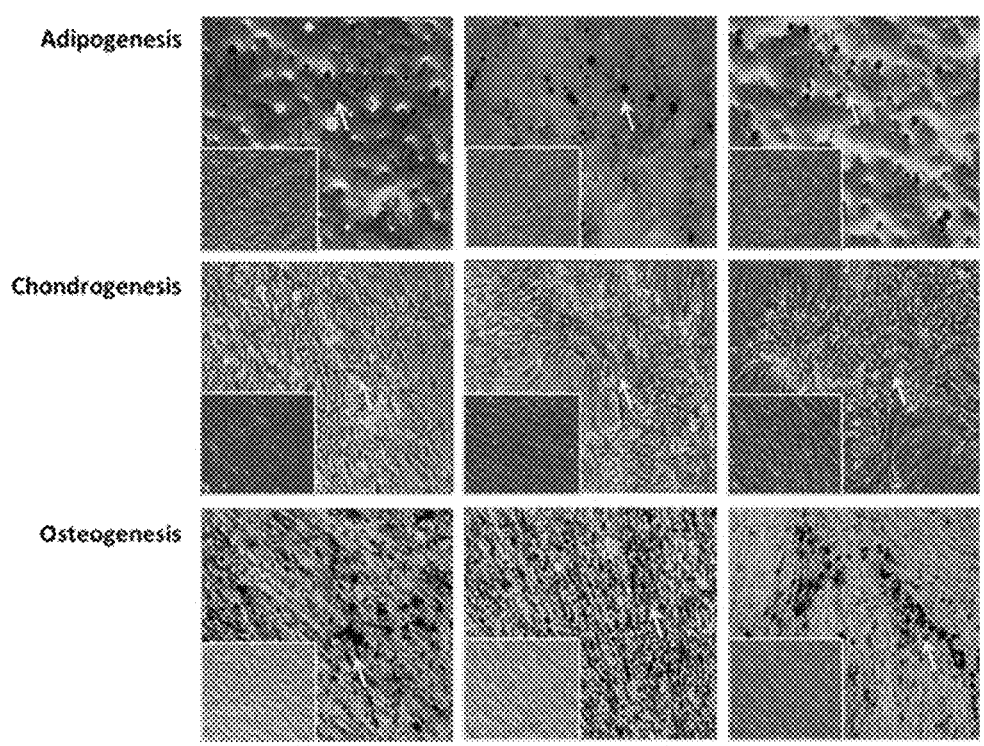
FIG. 10 refers to the in vitro differentiation of dental stem cells. The phase contrast images at 20× magnification. Adipogenic differentiation, lipid droplet stained red (arrow); chondrogenic differentiation, proteoglycan stained blue (arrow); osteogenic differentiation, calcium mineralized stained black (arrow). Inset: control of each staining for each type of dental stem cells.

The expression of pluripotent stem cells markers, stem cells markers, endoderm markers, mesoderm markers and ectoderm markers of dental stem cells were verified by the reverse transcriptase polymerase chain reaction (RT-PCR) analysis (refer FIG. 10). Based on the observations, SCDs, DPSCs and PDLSCs demonstrated high expression (+++) of the pluripotent stem cells markers namely Nanog and Oct 4. Sox 2 showed very high expression (++++) for DPSCs, high (+++) and moderate (++) expressions for SCDs and PDLSCs respectively. The expressions of stem cells markers ABCG2 were very high (++++) for both SCDs and DPSCs compared to PDLSCs. Rex 1 showed moderate expression (++) for SCDs, DPSCs and PDLSCs. The expressions of endoderm marker (BMP 4) were very high (++++) for SCDs and high (+++) for DPSCs and PDLSCs. In addition, SCDs showed very high expressions (++++) of mesoderm markers (MSX 1, HAND 1 and Gata 2) compared to DPSCs and PDLSCs. The results revealed no expressions (−) of Osterix for SCDs DPSCs, and PDLSCs. The expressions of ectoderm markers namely βIII Tubulin, Nestin, NUUR 1, NF, KRT 8 and KRT 15 for SCDs, DPSCs, and PDLSCs were also observed. SCDs, DPSCs, and PDLSCs displayed very high expressions (++++) of βIII Tubulin, Krt 8, and Krt 15 whereas moderate expressions (++) of Pax 6. The expressions of Nestin were very high (++++), high (+++) and moderate (++) for SCDs, DPSCs and PDLSCs, respectively. SCDs showed high expressions (+++) of NF and Nurr 1 compared to DPSCs with low (+) expressions. There were no expressions (−) of NF and Nurr 1 observed for PDLSCs.

Example 11

Differential of Each Dental Pulp Stem Cells Isolated from Permanent (DPSCs), Deciduous (SCDs) and Periodontal Ligament Stem Cells (PDLSCs) at Subculture 3 which is also known as Finish Product (Refer FIG. 10).

Adipogenic differentiation—The cells were seeded in 6-wells plate (BD Falcon), grown until 80% confluence in an induction media containing DMEM-KO (Invitrogen) supplemented with 10% FBS (Hyclone, USA), 1% glutamax, 10 µg/ml insulin, 200 µM indomethacin, 0.5 mM 3-isobuthyl-1-methyxanthine and 1 µM dexamethasone sodium phosphate. The induction media was changed twice a week up to a period of 21 days. The lipid droplets were stained with Oil Red O. For the staining, the cells were fixed using 4% of paraformaldehyde (PFA) for 35 minutes at room temperature ($23\pm1°$ C.). The cells were gently washed twice using 1 ml DPBS ($-Ca^{2+}$, $-Mg^{2+}$, Invitrogen). Then the cells were again gently washed using diethylpyrocarbonate-treated water (DEPC, Merck, Malaysia) twice. Oil Red O working solution (1 ml) were gently added to the well and incubated for 60 minutes at room temperature ($23\pm1°$ C.). Then, the cells were gently washed with DEPC-treated water for three times. The cells were observed under microscope for the presence of adipocyte containing lipid droplets which will be stained red. Chondrogenic differentiation—The cells were seeded in 6-wells plate (BD Falcon) and grown in growth media until reach 80% of confluence. The medium were then changed to chondrogenic media which comprises of DMEM-KO (Invitrogen), supplemented with 10% of FBS (Hyclone, USA), 1% of glutamax (Invitrogen), 5.35 µg/ml of linoleic acid, 10 µg/ml of L-ascorbic 2 phosphate, 1.25 µg/ml of bovine serum albumin, 10 µg/ml insulin and 1.0 µg/ml of dexamethasone sodium phosphate. The media was changed twice a week up to 21 days. The accumulation of sulfate proteoglycan was demonstrated using Alcian Blue staining. For the staining, the cells were fixed using 4% PFA for 10 minutes at room temperature ($23\pm1°$ C.). The cells were then washed twice using 1 ml of DPBS ($-Ca2+$, $-Mg2+$, Invitrogen). One ml of Alcian Blue working solution with a of pH 2.5 was added into the wells and left at room temperature ($23\pm1°$ C.) for 50 minutes. Then, the cells were washed using tap water for 3 times followed by another twice rinses using $ddH_2O$. The cells were observed under microscope for the presence of sulfate proteoglycan accumulation which will be stained blue. Osteogenic differentiation—The cells were seeded in 6-wells plate (BD Falcon) and grown in growth media until reach 80% of confluence. The medium were then changed to osteogenic induction media containing DMEM-KO (Invitrogen), supplemented with 10% of FBS (Hyclone, USA), 0.1 µM of dexamethasone sodium phosphate, 0.2 mM L-ascorbic 2 phosphate, 1% of glutamax (Invitrogen) and 10 mM of β-glycero-2-phosphate. The media was changed twice a week for 21 days. The mineralization of extracellular matrix was stained with Von Kossa staining. For the staining, the cells were fixed with 4% PFA for 15 minutes at room temperature ($23\pm1°$ C.). The cells were washed twice using 1 ml of ddH2O. Then 1 ml of 1% silver nitrate was added into the wells and was exposed under bright light for at least 60 minutes at room temperature ($23\pm1°$ C.). Then, the cells were washed once using ddH2O and the cells were observed under microscope for the presence of calcium deposit which will be stained black. All the chemicals were purchased from Sigma Aldrich unless stated.

Dental stem cells were differentiated into adipogenic, chondrogenic and osteogenic at passage 3 (FIG. 11). Detection of adipogenic differentiation was confirmed by Oil Red O staining for accumulation of lipid droplets. All control groups showed no accumulation of lipid droplet compared to the test group. Alcian blue staining shown positive with the detection of proteoglycan accumulation, indicating chondrgenic differentiation. In contrast, the control group did not take up any stain. Dental stem cells demonstrated the mineralization of calcium, stained in black by Von Kossa.

Example 12

Immmunophenotyping Analysis of Each Dental Pulp Stem Cells Isolated from Permanent (DPSCs), Deciduous (SCDs) and Periodontal Ligament Stem Cells (PDLSCs) at Subculture 3 which is also known as Finish Product The immunophenotyping was done at passage 3. The cells were harvested by utilizing 0.05% EDTA-Trypsin (Invitrogen) when it reaches 80% to 90% confluence, and resuspended in DPBS ($-Ca^{2+}$, $-Mg^{2+}$, Invitrogen). A total of $1.5\times10^6$ cells were suspended and incubated with the labeled antibodies in a dark room for one hour at 37° C. The antibodies used to mark the cell surface epitopes were CD34-phycoerythrin, CD44-phycoerythrin, CD73-phycoerythrin, CD90-phycoerythrin, CD166-phycoerythrin and, CD45-Fluoro-isothyocyanate, 7-AAD, HLA-DR-FITC, Notch 1-Fluoro-isothyocyanate, Slug-Fluoro-isothyocyanate, BarX 1-Fluoro-isothyocyanate, Fibronectin-Fluoro-isothyocyanate and p75 NGF Receptor-Fluoro-isothyocyanate. The immunophenotype analyses were standardized against negative control cells which were incubated with isotype-specific Immunoglobulin G1-phycoerythrin (IgG1-PE) and Immunoglobulin G1-Fluoro-isothyocyanate (IgG1-FITC). At least 10,000 events were acquired using a flow cytometer (Guava Technologies) and the results were analyzed using Cytosoft, Version 5.2 Guava Technologies. All the antibodies were purchased from BD Biosciences unless stated. Identification of SCDs, DPSCs and PDLSCs by cell surface markers, cellular differentiation (CD) antigens, which denote the expression of particular proteins associated with genomic activity related to a particular differentiation state of the cell were done using flow cytometry. The fluorescence-activated cell sorting (FACS) analysis showed that over 90% of cells were positive for the mesenchymal stem cell markers namely CD44, CD73, CD90, and CD166 (FIG. 4). The expression of CD 44 was lower in SCDs ($93.33\pm1.83$) compared to DPSC ($94.85\pm1.28$) and PDLSCs ($98.64\pm1.20$). However, SCDs showed higher expression of CD 73 ($99.30\pm0.81$), CD 90 ($98.78\pm1.63$), and CD 166 ($97.94\pm1.61$) compared to DPSCs ($98.87\pm1.24$; $97.67\pm1.40$;

96.57±0.98) and PDLSCs (98.51±1.17; 97.68±0.49; 70.32±4.93), respectively. The presence of CD34 (0.08±0.03; 0.24±0.23; 0.10±0.14), CD45 (0.02±0.01; 0; 0.24±0.09) and HLA-DR (0; 0.17±0.09; 0.09±0.13) were found to be less than 1% in SCDs, DPSCs and PDLSCs. The expression of Notch 1 in SCDs (99.23 0.32) and PDLSCs (97.76±2.46) revealed highly expressed compared to DPSC (74.60±3.63). Fibronectin was found to be 51.65±2.05 in SCDs, 53.74±2.12 in DPSCs and 66.20±0.19 in PDLSCs, while the expression of Barx 1 was 76.89±2.06, 67.61±1.35 and 83.72±1.87 respectively. The percentage of positive cell population of SLUG was higher for DPSCs (71.30±0.56) compared to 66.88±0.18 in SCDs and 66.92±1.27 in PDLSCs. Nevertheless, the expression of p75 NGF in DPSCs (71.74±0.42) was lower compared to SCDs (98.78±0.39) and PDLSCs (97.75±2.89).

The invention claimed is:

1. A method for isolating and proliferating at least one type of precursor cell from dental origin from a single donor, said method comprising the following steps:
   a) isolating the at least one type of precursor cell from dental origin of a single donor in a sample collection media and preparing a primary stock culture, wherein the sample collection media comprises DMEM media in an amount ranging between 66.5% and 90.5%, Human Albumin Phosphate in an amount ranging between 5% and 20%, Penicillin-Streptomycin in an amount ranging between 1% and 3%, fungizone in an amount ranging between 1% and 3%, and insulin-transferrin-selenium in an amount ranging between 2.5% and 7.5%;
   b) proliferating the primary stock culture sequentially to obtain a first, second and third sub-cultured stocks with cell counts ranging between $5\times10^6$ cells and $10\times10^6$ cells, $20\times10^6$ cells and $400\times10^6$ cells, $150\times10^6$ and $300\times10^6$ cells respectively; and
   c) harvesting and cryo-preserving the at least one type of precursor cell from the third subculture to obtain a precursor cell population capable of being used for cell transplantation,
   wherein the dental origin of the precursor cell is at least one selected from the group consisting of pulp, apical papilla, and periodontal ligament, and wherein the at least one type of precursor cell is at least one selected from the group consisting of mesenchymal stem cells, ecto-mesenchymal cells, neural stem cells, dental progenitor cells, and CD117+ cells.

2. The method as claimed in claim 1, wherein the method step of preparing the primary stock culture from the at least one type of precursor cell comprises steps of:
   a. mincing a dental tissue to obtain a desired size ranging between 0.5 mm$^3$ and 2.5 mm$^3$;
   b. digesting the minced dental tissue by incubating it in a mixture of Collagenase Type-IV Stock Solution and Knockout-Dulbecco's Modified Eagle Medium at 37° C. in 5% humidified $CO_2$ incubator for a time period ranging between 15 minutes and 30 minutes;
   c. diluting the digested mixture from step (b) with Dental Pulp Complete Culture Media 1 (DP-CCM1) comprising DMEM-KO at 73%, fetal bovine serum at 20%, penicillin-streptomycin at 5%, and glutamax at 2%
   d. centrifuging the diluted mixture from step (c) to obtain a pellet;
   e. re-suspending the pellet from step (d) in a fresh Dental Pulp Complete Culture Media 1, and
   f. culturing the cells obtained from the pellet of step (e) in incubator till the confluency of the cells reaches between 80% and 85%.

3. The method as claimed in claim 2, wherein the desired size is between 0.8 mm$^3$ and 1.5 mm$^3$.

4. The method as claimed in claim 1, wherein the method step of sequential sub-culturing comprises steps of:
   a. removing the conditioned media from the preceding primary stock culture;
   b. rinsing the stock culture with Dulbecco's Phosphate Buffered Saline (DPBS);
   c. trypsinizing the stock culture with Trypsin-EDTA in an amount ranging between 0.5 ml and 2.5 ml;
   d. adding Dental Pulp Complete Culture Media 2 (DP-CCM2) comprising DMEM-KO at 83%, fetal bovine serum at 10%, penicillin-streptomycin at 5%, and glutamax at 2% been;
   e. centrifuging the resulting cell suspension at 1200 rpm for 6 minutes at room temperature (18° C.±2° C.) to obtain a pellet;
   f. reconstituting the cell suspension by re-suspending the pellet in fresh DP-CCM2;
   g. dividing the resulting cell suspension from step (f) into a quality control test sample, a retention cell culture and an expansion cell culture;
   h. subjecting the expansion cell culture to sub-culturing in DP-CCM2 in an amount ranging between 800 cm$^2$ and 2500 cm$^2$; and
   i. incubating the cells at 37° C. in 5% humidified $CO_2$ incubator till the confluency of the cells reaches between 80% and 85%.

5. The method as claimed in claim 1, wherein the method step of cryo-preserving comprises steps of:
   a. adding Cell Freezing Media to the cells from the third stock culture, wherein the Cell Freezing Media comprises DMSO at 10%, human serum albumin at 10%, penicillin-streptomycin at 5%, and glutamax at 2%;
   b. centrifuging the resultant mixture to obtain a pellet;
   c. re-suspending the pellet in a fresh Cell Freezing Media;
   d. sealing the reconstituted Cell Freezing Media based cell suspension in a cryobag;
   e. transferring the cryobag to a Controlled Rate Freezer wherein the temperature is reduced gradually at 1° C. per minute till it reaches −80° C.; and
   f. transferring the cryobag to vapour phase of liquid nitrogen storage freezer for storage purposes.

* * * * *